United States Patent [19]

Cho

[11] Patent Number: 5,109,830
[45] Date of Patent: May 5, 1992

[54] APPARATUS FOR NAVIGATION OF BODY CAVITIES

[75] Inventor: George Cho, Sudbury, Mass.

[73] Assignee: Candela Laser Corporation, Wayland, Mass.

[21] Appl. No.: 507,388

[22] Filed: Apr. 10, 1990

[51] Int. Cl.⁵ .............................................. A61B 1/06
[52] U.S. Cl. ......................................... 128/4; 604/95; 604/281; 128/772; 606/7
[58] Field of Search ........................ 604/95, 164, 281; 128/4, 6, 398, 657, 658, 772; 606/6, 7, 13–16

[56] References Cited

U.S. PATENT DOCUMENTS

| | | |
|---|---|---|
| 1,060,665 | 5/1913 | Bell ........................................ 604/281 |
| 3,043,309 | 7/1962 | McCarthy . |
| 3,452,742 | 7/1969 | Muller . |
| 3,539,034 | 11/1970 | Tafeen . |
| 3,605,725 | 9/1971 | Bentov . |
| 3,674,014 | 7/1972 | Tillander . |
| 3,680,562 | 8/1972 | Wittes et al. . |
| 3,856,009 | 12/1974 | Winnie . |
| 3,860,006 | 1/1975 | Patel . |
| 3,920,023 | 11/1975 | Dye et al. . |
| 4,033,331 | 7/1977 | Guss et al. . |
| 4,146,019 | 3/1979 | Bass et al. .............................. 128/6 |
| 4,176,662 | 12/1979 | Fraser ..................................... 128/6 |
| 4,249,533 | 2/1981 | Komiya ................................. 606/15 |
| 4,367,729 | 1/1983 | Ogiu ...................................... 606/15 |
| 4,445,892 | 5/1984 | Hussein et al. ......................... 606/7 |
| 4,461,283 | 7/1984 | Doi ........................................ 606/15 |
| 4,512,765 | 4/1985 | Muto ..................................... 604/281 |
| 4,568,338 | 2/1986 | Todd ..................................... 604/281 |
| 4,601,283 | 7/1986 | Chikama ................................ 128/4 |
| 4,657,014 | 4/1987 | Edelman et al. ...................... 606/15 |
| 4,738,667 | 4/1988 | Galloway ............................. 604/281 |
| 4,758,222 | 7/1988 | McCoy ................................. 604/95 |
| 4,765,330 | 8/1988 | Bach ..................................... 606/14 |
| 4,782,819 | 11/1988 | Adair ..................................... 128/6 |
| 4,800,870 | 1/1989 | Reid, Jr. ................................. 128/6 |
| 4,807,626 | 2/1989 | McGirr ................................. 604/281 |
| 4,869,246 | 9/1989 | Adair ..................................... 606/14 |
| 4,882,777 | 11/1989 | Narula ................................... 604/281 |
| 4,925,445 | 5/1990 | Sakamoto et al. ................... 128/772 |

FOREIGN PATENT DOCUMENTS

| | | | |
|---|---|---|---|
| 88/08726 | 11/1988 | PCT Int'l Appl. ................. 604/164 |
| 89/01755 | 3/1989 | PCT Int'l Appl. .................... 604/96 |

OTHER PUBLICATIONS

USCI, Cardiovascular Catheters and Accessories Sales Catalogue, ©1967, p. 41.

Primary Examiner—Stephen C. Pellegrino
Assistant Examiner—Ralph A. Lewis
Attorney, Agent, or Firm—Hamilton, Brook, Smith & Reynolds

[57] ABSTRACT

An apparatus for navigation of body cavities is comprised of an inner element and an outer element that surrounds the inner element. The inner element has a memorized preformed shape that it assumes when it is not disposed within the outer element. When in the outer element, the inner element is straightened by the rigidity of the outer element. The preformed shape of the inner element is adjustable. This preformed shape may be exploited to navigate branches and curves in the body cavities. The inner element may be a catheter or laser fiber, and the outer element may be a catheter or sheath. When the inner element is a catheter, the catheter may contain a shape retaining element such as a spring wire that enables it to memorize the preformed shape.

23 Claims, 3 Drawing Sheets

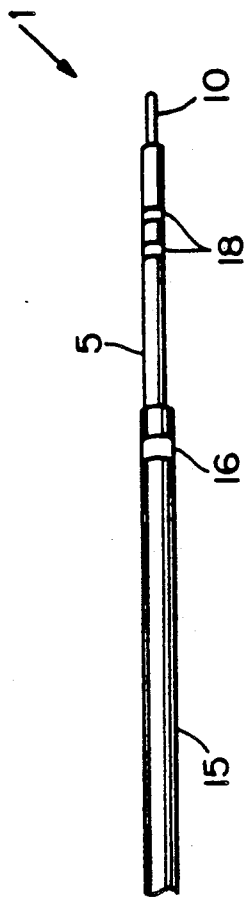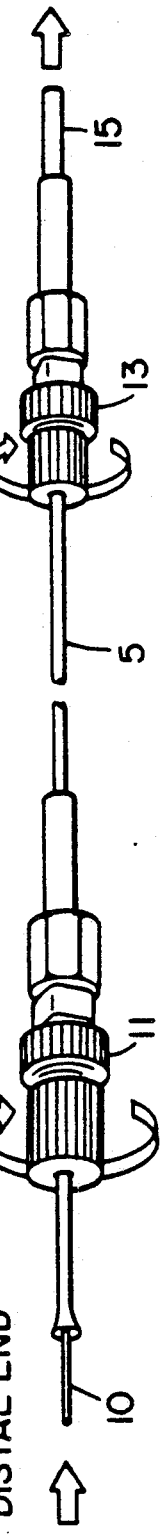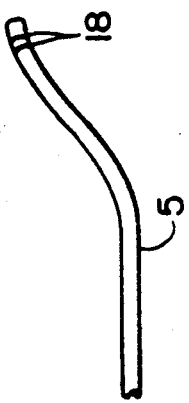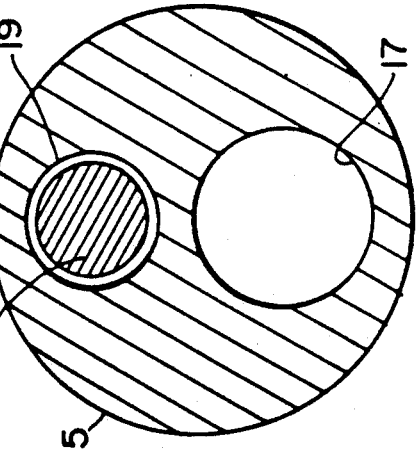

APPARATUS FOR NAVIGATION OF BODY CAVITIES

BACKGROUND OF THE INVENTION

Medical procedures often require the insertion of medical devices such as a catheter or optical fiber into a patient. To properly use such medical devices, it is necessary to be able to navigate the devices through body cavities and channels. Current systems generally employ straight catheters or fibers that are flexible enough to conform to the body cavity in which they are disposed. Navigation is realized by pushing the devices forward or pulling them backward from the proximate end. As the devices are moved, the navigator of the devices must rely solely on the flexibility of the devices to navigate through branches and curves in the body. Another form of catheter, such as that of U.S. Pat. No. 4,802,461, has a controllable flexible tip at the distal end of a straight catheter. Deformation of the tip can be caused through control wires operated at the proximal end.

SUMMARY OF THE INVENTION

In accordance with one embodiment of the present invention, a deformable catheter exhibits memory of a preformed shape. The catheter is comprised of a first lumen and a second lumen. In the second lumen a shape retaining element that dictates the shape of the catheter element is disposed. The shape retaining element is configurable into the preformed shape. This preformed shape is memorized by the shape retaining element so that the shape retaining element returns to the preformed shape in the absence of sufficient countering force to prevent it from assuming the preformed shape. The countering force is provided by an outer catheter.

In one embodiment, a laser transmitting optical fiber is disposed within a lumen of the catheter. It is preferred that the catheter be configured so that only a distal tip of the catheter is curved. The remainder of the catheter is straight. This preferred shape may be altered by the application of significant force to the curved portion of the catheter before it is introduced into the outer catheter. The application of the significant force produces a new preformed shape at the distal end of the catheter. This new preformed shape is, like the old preformed shape, memorized by the shape retaining element. By "memorized", it is meant that the distal end of the catheter always returns to the preformed shape unless a restraining external force prevents it from assuming the preformed shape. A good candidate for the shape retaining element is a spring wire.

More than one wire element or shape retaining element may be disposed within the catheter. To that end multiple lumens may be employed within the first catheter and the shape retaining elements placed within these lumens. Each of the shape retaining elements should have a significant modulus of elasticity. In a preferred embodiment the shape retaining elements are configured so that the inner catheter is curved into a substantially "S" shape.

This preformed catheter is designed to be used in a catheter system. In particular, the catheter system is comprised of the previously described deformable catheter and a second catheter in which the deformable catheter is slideably disposed. The second catheter has sufficient rigidity to overcome and straighten the preformed shape of the shape retaining element (i.e. wire element) that is in the first catheter. The preformed shape, nevertheless, returns to the first catheter when the first catheter is not disposed within the second catheter. As such, the second catheter serves to temporarily straighten the first catheter without permanently altering the preformed shape. This catheter system is ideal for use in such procedures as the destruction of calculi and laser surgery.

This catheter system enhances the navigation ability of the inner catheter by exploiting the preformed shape of the inner catheter. In particular, the curved portion of the catheter may be positioned relative to the outer catheter so that the curved portion of the inner catheter is exposed. If fluoroscopic techniques are used for navigation, radiopaque rings may be put on the inner catheter and outer catheter to help locate the catheters, positions inside the patent.

In accordance with another embodiment of the present invention an apparatus for carrying laser energy is comprised of an optical fiber. The optical fiber serves as the transmitting medium to carry the laser energy. It has a distal end that is bent into a preformed curved shape. To assure that the fiber does not break, a strengthening agent is applied to at least the distal end of the fiber. It is preferred that the strengthening agent be one of several materials. In particular, it is preferred that the strengthening agent be a plastic material, such as polyimide or a high density polyethylene or polytetraflouroethylene (i.e. "TEFLON"). It may also be metal tubing such as stainless steel.

The strengthened fiber is disposed within an outer sheath that also helps to protect the fiber. The outer sheath serves, in large part, the same role that is served by the second catheter in the previously described embodiment. In particular, the outer sheath has sufficient rigidity to straighten the optical fiber while the optical fiber is disposed within the outer sheath. Nevertheless, when the optical fiber is not disposed within the outer sheath, the optical fiber returns to its preformed curved shape. As such, it can be said that the optical fiber has memorized the preformed curve shape. In the preferred embodiment, this preformed curve shape represents a substantially "S" shape.

By instilling a preformed shape into the optical fiber the navigability of the fiber is significantly enhanced. Typically, the fiber is delivered to the appropriate site in a duct of a patient by an endoscope. Once delivered to the site, the fiber may be moved relative to the outer sheath to expose a straight portion of the fiber. Once the straight portion is exposed the apparatus as a whole is moved forward in straight direction. On the other hand, if it is necessary for the fiber to move in a first lateral direction, the fiber is adjusted in position relative to its surrounding sheath such that a portion of fiber bending in the first lateral direction is exposed. This bent portion serves as a guide that aids in directing the apparatus in that first lateral direction. Similarly, the fiber may be adjusted so that a portion of the fiber oriented in a second lateral direction is exposed. The exposed portion of the fiber serves to aid in navigating the apparatus in the second lateral direction. The preformed shape of the inner catheter in the previously referenced catheter system aids in navigation in an analagous manner to the optical fiber.

BRIEF DESCRIPTION OF THE DRAWINGS

FIG. 1 depicts a catheter system.

FIG. 2 depicts the adapters employed in the catheter system.

FIG. 3 depicts an inner catheter of the catheter system.

FIG. 4 depicts the preferred preformed shape of the catheter.

DETAILED DESCRIPTION OF THE PREFERRED EMBODIMENT

Figure 5A:
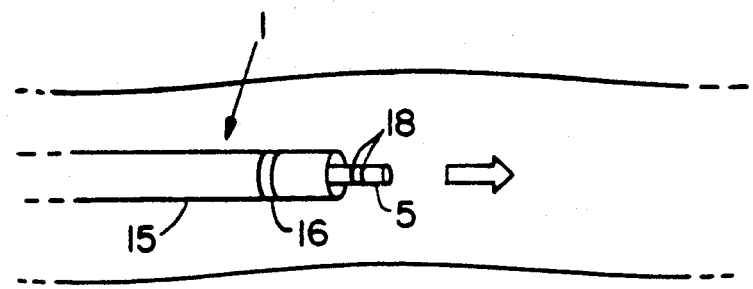
FIGS. 5a, 5b and 5c depict how the bent inner catheter aids in navigation within body cavities.

In accordance with one embodiment of the present invention, a catheter system 1 is comprised of an outer catheter 15 and an inner catheter 5. The inner catheter 5 is disposed within the outer catheter 15 so that it may slide relative to the outer catheter 15. The outer catheter 15 has an outer diameter of approximately 0.130 inch and an inner diameter of 0.078 inch. The inner catheter 5 has an outer diameter of 0.055 inch which allows it to readily fit and slide within the outer catheter 15. Each of the catheters 5 and 15 are made of material such as polytetrafluoroethylene ("TEFLON"), polyethylene or other materials commonly used in catheters.

Since the catheter system 1 is designed to be employed within the human body it is necessary to have a means for navigating the catheter system 1 within body cavities of the patient. Numerous techniques are available, but the present catheter system 1 is designed so that fluoroscopic techniques may be employed for navigation. To facilitate fluoroscopic navigation the outer catheter 15 has a ring 16 of radiopaque material positioned at its distal end. The inner catheter 5, likewise, has rings 18 of radiopaque material affixed to it, but it has two rings 15 as opposed to one ring 16 to distinguish the inner catheter 5 from the outer catheter 15. The radiopaque rings 16 and 18 must be employed because the materials of which the catheters 5 and 15 are made are not clearly visible with fluoroscopy.

It is desirable for the catheter system 1 to be able to carry laser energy, for many current medical procedures require a catheter capable of delivering laser energy. To facilitate such capabilities, the catheter system 1 has a lumen for carrying a laser fiber 10. The laser fiber 10 is made of materials that are known in the prior art. The coupling of the laser fiber 10 to a laser source is realized using conventional techniques.

FIG. 2 illustrates how adapters 11 and 13 interface the laser fiber 10, inner catheter 5, and outer catheter 15. Specifically, laser fiber 10 is disposed within an adapter 11 that interfaces the laser fiber 10 with the inner catheter 5. Once the laser fiber 10 is appropriately positioned relative to the inner catheter 5, the adapter 11 may be rotated to lock the laser fiber in position. A similar approach is adapted for positioning the inner catheter 5 relative to the outer catheter 15. An adapter 13 interfaces the two catheters 5 and 15 and locks the catheters in position relative to each other (by tightening a rotating portion of the adapter 13).

FIG. 3 shows a cross-sectional view of the inner catheter 5. As can be seen in FIG. 3, the inner catheter 5 has lumens 17 and 19. Additional lumens may be added for particular applications. FIG. 3 depicts a preferred embodiment in which two lumens are provided within the inner catheter 5. It should, nevertheless, be appreciated that embodiments having different numbers of lumens are intended to be encompassed within the scope of the present invention.

As mentioned previously, one of the lumens 17 is used by a laser fiber 10. The laser fiber 10 is disposed within the lumen 17 so that it may slide back and forth relative to the catheter 5. The lumen 17 has a diameter of approximately 0.022 inch. The other lumen 19 is occupied by a spring wire 12 that has a very high modulus of elasticity (which implies that it is very rigid). The wire has an outer diameter of about 0.018 inch. This spring wire 12, however, may be replaced by two spring wires both having a diameter of 0.014 inch.

The spring wire 12 enables the inner catheter 5 to be formed into a preformed shape. As such, the inner catheter 5 may assume curved shapes. The preformed shape is memorized by the spring wire 12 so that the spring wire assumes the memorized shape absent the exertion of constraining forces. The outer catheter 15 has sufficient rigidity and strength to overcome the preformed shape of the spring wire 12. As a result, the inner catheter 5 is straight when disposed within the outer catheter 15. Nevertheless, the straightening of the inner catheter 5 achieved by the outer catheter is not permanent. To permanently alter the shape, significant force must be applied to the inner catheter 5. Once the shape of the inner catheter 5 has been permanently altered, the new shape is memorized like the previously memorized shape. This capability provides a flexibility to the inner catheter 5 that allows the inner catheter 5 to assume any of many different possible shapes.

Figure 5B:
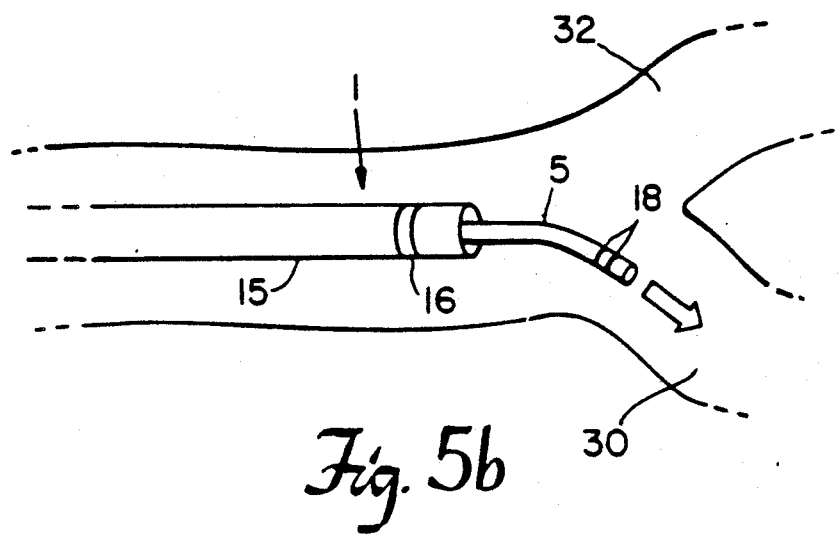
Figure 5C:
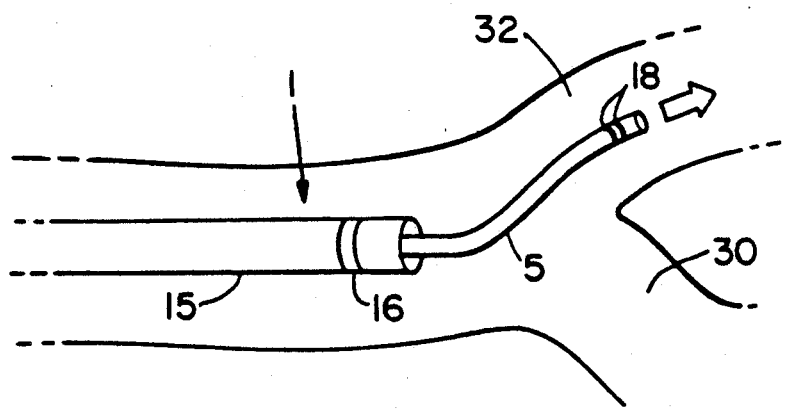

One preferred preformed shape in which the inner catheter 5 may be bent is depicted in FIG. 4. This shape is a substantially "S" shape. The "S" shape allows the inner catheter to be navigated in any given lateral direction, and hence, greatly enhances the ability to navigate within body cavities of patients. FIGS. 5a, 5b and 5c illustrate more explicitly how the "S" shape shown in FIG. 4 is useful in navigating within body cavities. In these figures, the optical fiber 10 is retracted relative the inner catheters. FIG. 5a illustrates how the catheter system may be employed within a body cavity to navigate in a straight direction. Specifically, the inner catheter 5 is moved relative to the outer catheter 15 so that only the leading most portion of the inner catheter 5 is exposed. This leading exposed portion is oriented in a straight direction so that the catheter system may be moved in the straight direction by moving the outer catheter 15 together with the inner catheter 5 as a unit.

The catheter system 1, however, is not limited through motion in a single straight direction. Rather, it may be, likewise, moved in either lateral direction (i.e. towards the right or left). FIG. 5b illustrates how the catheter system 1 may be moved in a right-hand lateral direction. More specifically, FIG. 5b shows how the catheter system may be oriented down a right-hand fork 30 of a body cavity. To move down this right hand fork 30, the inner catheter 5 is exposed to reveal only a right-hand curving portion of it. The entire catheter system 1 is then be moved forward which results in the inner catheter 5 forking to the right. The inner catheter 5 creates a steering to the right-hand fork 30 so that the outer catheter 15 tend towards the right-hand direction and conforms to the shape of the right hand fork 30 of the body cavity. The outer catheter 15 is designed to be flexible enough to conform to the shape of the body cavities in which it travels.

FIG. 5c illustrates how the catheter system can be navigated in the other lateral direction referred to as the left-hand direction. To achieve left hand navigation an additional portion of the inner catheter 5 is exposed relative to the outer catheter 15. This additional portion is oriented primarily in a left-hand direction. The catheter system is, thus, moved as previously described which results in movement along the left hand branch 32 of the body cavity.

Figure 6:
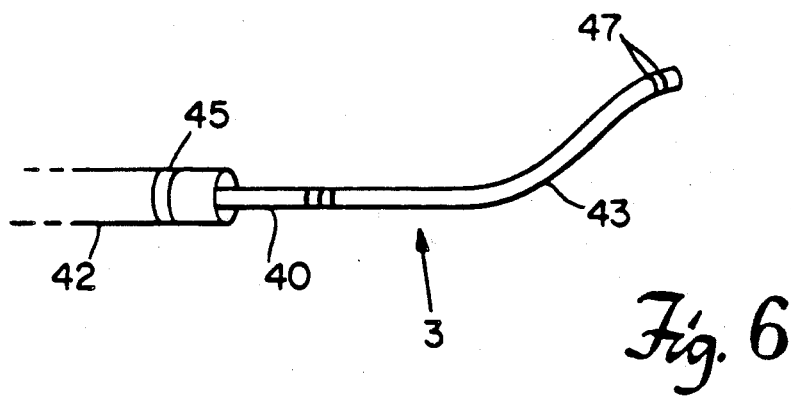
FIG. 6 depicts a optical fiber system.

FIG. 6 depicts an alternative embodiment designed for use in body cavities having a small diameter. In this alternative embodiment, a laser fiber 40 as opposed to an inner catheter is bent into a preformed shape. A preferred preformed shape for the laser fiber 40 is the "S" shape shown in FIG. 6. The laser fiber is covered with a strengthening agent 43. Good candidates for a strengthening agent 43 are plastic materials such as polyimide. Another good candidate is stainless steel which has the additional benefit of being radiopaque. The strengthening agent 43 serves to enhance the strength of the fiber 40 so that it is unlikely that the fiber will break within the human body. It should be noted that in this embodiment the fiber 40 is permanently formed into the bent preformed shape. The shape may be realized when forming the optical fiber 40 by subjecting it to heat using known techniques for bending glass fibers.

The strengthened optical fiber 40 is disposed within an outer catheter sheath 42. The outer sheath 42 serves much the same role as the outer catheter 15 in the previously described embodiment. It has sufficient rigidity to overcome the preformed shape of the laser fiber 40, but it does not exert such extensive forces so that the shape of the fiber 40 is permanently lost or broken. If the outer sheath 42 is made of a material that is not radiopaque, a ring 45 of radiopaque material is situated on the outer sheath 42 to enable fluoroscopic navigation. Similarly multiple rings 47 and 49 are employed on the strengthened portion of the laser fiber 40.

The major advantages of this fiber embodiment include that it is a very simplified apparatus that will cost little to produce and that is simple to use. Another major advantage is that this embodiment may be realized with a very small diameter. In particular, the optical fiber 40 has a diameter of about 200 microns. The outer sheath has an inside diameter of 0.020-0.024 inches and an outer diameter of 0.026-0.030 inches. This small diameter enables this embodiment to enter body cavities having small diameters, such as, arteries, the ureter and the common bile duct. It should be appreciated, however, that different diameters of fibers may be used.

Navigation of this embodiment resembles navigation such as described in the previous embodiment. In particular, the optical fiber 40 is manipulated into an appropriate position relative to the outer sheath 42. So that a portion of the optical fiber 40 oriented in the appropriate direction is exposed. The fiber 40 and outer sheath 42 are then moved in the appropriate direction. The fiber 40 need not be shaped in the "S" shape shown in FIG. 3; rather, the fiber 40 may be formed into a number of other different shapes.

Figure 7:
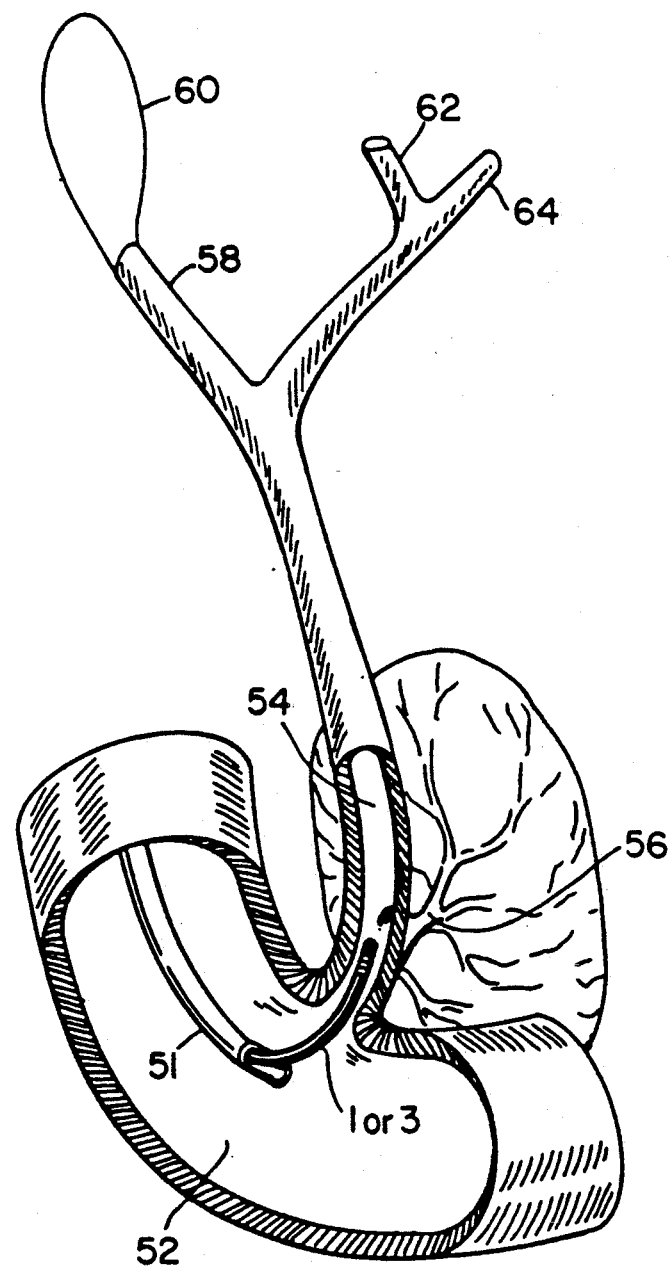
FIG. 7 depicts portions of a human anatomy which the catheter system or optical fiber system may be readily navigated.

FIG. 7 shows exemplary portions of the human anatomy in which the catheter system 1 or the optical fiber system 3 may be disposed. Specifically, they may be introduced via duodenoscope 51 into the duodenum 52. From the duodenum 52, the systems 1, 3 may be moved into the common bile duct 54. Once in the common bile duct 54, they may be directed down the pancreatic duct 56 or navigated further up the common bile duct 54 to the cystic duct 58 that leads to the gall bladder 60. Still further, they also may be navigated to the left heptic duct 64 or the right heptic duct 62.

FIG. 7 shows only a potential sampling of the body cavities in which the embodiments described herein may be employed. The embodiments may also be employed in many other different portions of the body. In general, these embodiments are able to more readily be navigated within the human body to reach portions of the body that were previously difficult to reach.

While the invention has been particularly shown and described with reference to preferred embodiments thereof, it will be understood by those skilled in the art that various changes in form and details may be made without departing from the spirit and scope of the invention as defined in appended claims. For instance shape retaining elements other than a spring wire may be used such as a rigid plastic material and a wide spectrum of different materials may be employed for the catheters and the outer sheath.

I claim:

1. A catheter apparatus comprising:
   an outer catheter; and
   an inner expansion having a preformed substantially "S" shape and comprising an optical fiber capable of carrying laser energy, wherein the inner extension memorizes the preformed shape so that it returns to the preformed shape absent application of sufficient force, the inner extension being slidable within the outer catheter such that within the outer catheter the inner extension follows the shape of the outer catheter while portions of the inner extension outside the outer catheter assume the preformed shape, an extending of the inner extension from the outer catheter allowing a variable bend at a distal end of the apparatus for guiding the apparatus through body lumens.

2. A catheter apparatus as recited in claim 1 wherein the inner extension is configured in the preformed shape such that a distal tip of the extension is bent and a remainder of the inner extension is straight.

3. A catheter apparatus as recited in claim 1 wherein the preformed shape may be altered by application of significant force to the inner extension to create a new preformed shape that is memorized.

4. A catheter apparatus as recited in claim 1 wherein the inner extension has a shape retaining element comprising a spring wire.

5. A catheter apparatus as recited in claim 1 wherein the inner extension has a shape retaining element comprising a rigid plastic material.

6. An apparatus, comprising:
   (a) a first catheter having a first lumen and having at least one additional lumen in which a shape retaining element is disposed, said shape retaining element being configured in a preformed substantially "S" shape that absent exertion of external stress on the first catheter dictates the shape of the first catheter;
   (b) a second catheter in which the first catheter is slideably disposed such that the second catheter has sufficient rigidity to overcome and straighten the preformed shape of the shape retaining element within the first catheter when the first catheter is disposed within the second catheter, but said preformed shape returning to the shape retaining element when the first catheter is not disposed within the second catheter; and (c) an optical fiber disposed within the first lumen of the first catheter for carrying laser energy.

7. An apparatus as recited in claim 6 wherein the said shape retaining element comprises a wire guide having a significant modulus of elasticity.

8. An apparatus as recited in claim 7 wherein said wire guide is a spring wire.

9. An apparatus as recited in claim 6 wherein the preformed shape of the shape retaining element may be reconfigured to generate a new preformed shape.

10. An apparatus as recited in claim 6 wherein the apparatus is part of an endoscope for positioning the first catheter and the second catheter in a duct of a patient.

11. A catheter system for internal use in a patient, comprising:

(a) an inner catheter comprising:
   (1) a first lumen in which a laser optical fiber is disposed, said fiber being used to carry laser energy;
   (2) a second lumen in which is disposed a spring wire configured into a predetermined substantially "S" shape that the spring wire assumes absent constraining forces that prevent it from assuming the predetermined shape, said spring wire dictating the shape of the inner catheter; and (b) an outer catheter in which the inner catheter is slideably disposed, said outer catheter exerting forces on portions of the spring wire disposed within it that prevent the spring wire from assuming the predetermined shape.

12. A catheter system as recited in claim 11 wherein the predetermined shape of the spring wire is reconfigurable into a new predetermined shape upon the application of significant force.

13. A catheter system as recited in claim 11 further comprising radiopaque material situated at a distal end of the inner catheter to facilitate fluoroscopic navigation of the inner catheter.

14. A catheter system as recited in claim 11 further comprising radiopaque material situated at a distal end of the outer catheter to facilitate fluoroscopic navigation of the outer catheter.

15. A catheter system as recited in claim 11 wherein the spring wire is configured in a predetermined shape such that a distal end portion of the inner catheter is curved, whereas remaining portions of the inner catheter are straight.

16. An apparatus for carrying laser energy, comprising:

(a) an optical fiber for carrying laser energy, said fiber having a distal end that is bent into a preformed substantially "S" curved shape; and (b) an outer sheath that surrounds the optical fiber and within which the optical fiber is slidable, the outer sheath having sufficient rigidity to straighten the optical fiber while the optical fiber is disposed within the outer sheath, but said optical fiber returning to its preformed curved shape when not disposed within the outer sheath, the extension of the preformed fiber from the outer sheath allowing a variable bend at a distal end of the apparatus for guiding the apparatus through body lumens.

17. An apparatus as recited in claim 16 further comprising a strengthening agent for supporting the preformed shape of the fiber.

18. An apparatus as recited in claim 17 wherein the strengthening agent is a plastic material.

19. An apparatus as recited in claim 17 wherein the strengthening agent is radiopaque.

20. An apparatus as recited in claim 16 wherein the outer sheath is a catheter.

21. A method of navigating a catheter within a duct of a body, comprising the steps of:

(a) slideably disposing an inner catheter comprising a laser optical fiber within an outer catheter, wherein said inner catheter has a tip with a memorized preformed substantially "S" shape, and said outer catheter has sufficient rigidity to straighten portions of the inner catheter while the portions are disposed within the outer catheter;

(b) sliding the inner catheter relative to the outer catheter to expose a straight portion of the inner catheter so that both the inner catheter and the outer catheter are navigated in a forward direction; and (c) sliding the inner catheter relative to the outer catheter to expose a portion of the "S" shape of the inner catheter that is curved in a first lateral direction so that both of the catheters are navigated in the first lateral direction.

22. A method as recited in claim 21 further comprising the step of sliding the inner catheter relative to the outer catheter to expose a portion of the inner catheter that is curved in a second lateral direction so that both of the catheters are navigated in the second lateral direction.

23. A method of navigating a catheter within a duct of a body, comprising the steps of:

(a) slideably disposing an inner catheter within an outer catheter, wherein said inner catheter has a tip with a memorized preformed substantially "S" shape, and said outer catheter has sufficient rigidity to straighten portions of the inner catheter while the portions are disposed within the outer catheter;

(b) sliding the inner catheter relative to the outer catheter to expose a straight portion of the inner catheter so that both the inner catheter and the outer catheter are navigated in a forward direction; and (c) sliding the inner catheter relative to the outer catheter to expose a portion of the "S" shape of the inner catheter that is curved in a first lateral direction sot hat both of the catheters are navigated in the first lateral direction wherein the inner catheter and the outer catheter are part of an endoscope and the method further comprises the step of positioning the inner catheter and the outer catheter within a duct of a patient by control of the endoscope from a proximal end thereof.

* * * * *